United States Patent
Ding et al.

(10) Patent No.: US 11,837,329 B2
(45) Date of Patent: Dec. 5, 2023

(54) METHOD FOR CLASSIFYING MULTI-GRANULARITY BREAST CANCER GENES BASED ON DOUBLE SELF-ADAPTIVE NEIGHBORHOOD RADIUS

(71) Applicant: NANTONG UNIVERSITY, Nantong (CN)

(72) Inventors: Weiping Ding, Nantong (CN); Yu Geng, Nantong (CN); Jialu Ding, Nantong (CN); Hengrong Ju, Nantong (CN); Jiashuang Huang, Nantong (CN); Chun Cheng, Nantong (CN); Ying Sun, Nantong (CN); Yi Zhang, Nantong (CN); Ming Li, Nantong (CN); Tingzhen Qin, Nantong (CN); Xinjie Shen, Nantong (CN); Haipeng Wang, Nantong (CN)

(73) Assignee: NANTONG UNIVERSITY, Nantong (CN)

( * ) Notice: Subject to any disclaimer, the term of this patent is extended or adjusted under 35 U.S.C. 154(b) by 0 days.

(21) Appl. No.: 17/798,352

(22) PCT Filed: Feb. 22, 2022

(86) PCT No.: PCT/CN2022/077251
§ 371 (c)(1),
(2) Date: Aug. 9, 2022

(87) PCT Pub. No.: WO2023/005196
PCT Pub. Date: Feb. 2, 2023

(65) Prior Publication Data
US 2023/0197203 A1 Jun. 22, 2023

(30) Foreign Application Priority Data
Jul. 26, 2021 (CN) .......................... 202110845531.0

(51) Int. Cl.
*G16B 40/20* (2019.01)
*G16H 50/20* (2018.01)

(52) U.S. Cl.
CPC ............. *G16B 40/20* (2019.02); *G16H 50/20* (2018.01)

(58) Field of Classification Search
CPC .............................. G16B 40/20; G16H 50/20
See application file for complete search history.

(56) References Cited

U.S. PATENT DOCUMENTS

| 10,252,145 B2 * | 4/2019 | Tran ........................ G06V 40/28 |
| 10,381,105 B1 * | 8/2019 | Tran ........................ G16B 40/20 |

(Continued)

FOREIGN PATENT DOCUMENTS

| CN | 110023759 A | 7/2019 |
| CN | 110211638 A | 9/2019 |
| CN | 113838532 A | 12/2021 |

OTHER PUBLICATIONS

Cheng, Yi, et al.; Knowledge Discovery Model Based on Neighborhood Multi-granularity Rough Sets, Computer Science, vol. 46, No. 6, Jun. 15, 2019; pp. 224-230. (English Abstract).

(Continued)

*Primary Examiner* — Jay M. Patel
(74) *Attorney, Agent, or Firm* — HAUPTMAN HAM, LLP (57) ABSTRACT

A method for classifying multi-granularity breast cancer genes based on a double self-adaptive neighborhood radius includes large-scale gene locus data are read and normalized, and a data analysis is performed on the large-scale gene loci. An optimum value K is selected by adopting a combination of contour coefficients and a PCA dimensionality reduction visualization, and a model of information granulation is adjusted. A heuristic reduction algorithm is used to implement a multi-granularity attribute reduction of a self- (Continued)

adaptive neighborhood radius based on a cluster center distance and a multi-granularity attribute reduction of a neighborhood radius based on an attribute inclusion degree, and big data for breast cancer genes are classified and predicted by adopting a machine learning classification algorithm based on a SVM support vector machine.

4 Claims, 5 Drawing Sheets

(56) References Cited

U.S. PATENT DOCUMENTS

| | | | |
|---|---|---|---|
| 2004/0076984 A1* | 4/2004 | Eils .................. | G16B 40/20 435/6.13 |
| 2006/0177837 A1* | 8/2006 | Borozan ............ | G16B 50/00 435/6.1 |
| 2008/0313135 A1* | 12/2008 | Alexe ............... | G06F 16/285 |
| 2020/0135296 A1* | 4/2020 | Girshick ........... | G16B 20/40 |
| 2021/0174908 A1* | 6/2021 | Benjamin .......... | C07K 16/2863 |

OTHER PUBLICATIONS

International Search Report issued in International Application No. PCT/CN2022/077251; dated May 12, 2022; 5 pgs.
Written Opinion of the International Searching Authority issued in International Application No. PCT/CN2022/077251; dated May 12, 2022; 10 pgs.

* cited by examiner

METHOD FOR CLASSIFYING MULTI-GRANULARITY BREAST CANCER GENES BASED ON DOUBLE SELF-ADAPTIVE NEIGHBORHOOD RADIUS

RELATED APPLICATIONS

The present application is a U.S. National Phase of International Application Number PCT/CN2022/077251, filed Feb. 22, 2022, and claims priority to Chinese Application Number 202110845531.0, filed Jul. 26, 2021.

TECHNICAL FIELD

The present disclosure relates to the technical field of medical information intelligent processing, and in particular to a method for classifying multi-granularity breast cancer genes based on a double self-adaptive neighborhood radius.

BACKGROUND

Cancer is one of the most common gene disorders, and relevant medical studies have shown that lung cancer, skin cancer and breast cancer are closely related to genes. The occurrence of cancer can often be explained by gene mutation, if genetic materials are damaged without any repair, cancer cells will absorb the nutrients of normal cells and divide indefinitely, resulting in a decline of human function, where the cure rate for early cancer is higher, and the cure rate of the cancer cells after metastasis is lower, and early detection and early treatment is an optimum treatment at present. Gene detection is a non-destructive detection method that simultaneously detects thousands of gene loci through next-generation sequencing technology, it performs data analyses and related predictions on thousands of gene loci under big data, it analyzes and reduces big data for breast cancer genes from the perspective of feature engineering and granular calculation, and it classifies and predicts the big data for breast cancer genes through a machine learning classification algorithm, which has far-reaching significance for clinical treatment.

In recent years, in the "NCCN Guidelines for Breast Cancer", a high-throughput sequencing is recommended for the high-risk breast cancer populations with familial genetic predisposition to screen for genetic susceptibility genes, so as to prevent the cancer or guide the treatment, which fully shows that an individualized treatment and prevention based on the gene detection is a new direction for breast cancer. It is pointed out in the guidelines that for the high-risk breast cancer populations with familial genetic predisposition, the "NCCN Guidelines" recommends a breast self-examination, an enhanced imaging and corresponding serum tumor marker examinations, and a drug prevention, etc.

Although doctors can effectively analyze whether patients are the high-risk breast cancer patients through the analysis for gene data, there is too many gene data, and a new method is urgently needed to effectively reduce the redundant gene data in the classification information on breast cancer gene data, which reduces the analysis time of breast cancer data and improves the analysis efficiency and accuracy, and effectively performs an early screening of breast cancer, and has certain significance for the clinical treatment.

The detection is mainly used for a disease diagnosis. Through the method of gene diagnosis, not only the sensitivity is greatly improved, but also the results can be obtained in a short period of time, so as to identify the correct treatment method, to choose the correct drug, and to avoid adverse reactions caused by indiscriminate medication. The results of breast cancer gene detection can help the patients formulate correct treatment methods.

SUMMARY

The objective of the present disclosure is to provide a method for classifying multi-granularity breast cancer genes based on a double self-adaptive neighborhood radius, which solves the effects of existing effective methods for judging breast cancerization status, which is difficult to observe gene mutations for early diagnosis of breast cancer due to the over-high gene data dimension related to the breast cancer, and solves the problem of a difficult selection on a neighborhood radius in a neighborhood rough set through relations between the breast cancer gene data in combination with the double self-adaptive neighborhood radius, and can effectively remove noise and redundancy data by using an attribute reduction of a multi-granularity neighborhood rough set.

In order to achieve the above objective of the present disclosure, the following technical solution, which is a method for classifying multi-granularity breast cancer genes based on a double self-adaptive neighborhood radius, is adopted in the present disclosure. The method includes the following steps.

In S1, a data set for breast cancer genes is read, and data are converted into a four-tuple decision information system $S=(U, AT, V, f, \delta)$, and a neighborhood decision information system S is expressed as follows:

$S=(U, AT, V, f, \delta)$, where $U=\{x_1, x_2, x_3, \ldots, x_m\}$ represents an object set of detected patients in the data set for breast cancer genes, m represents a number of the detected patients with breast cancer genes; $C=\{a_1, a_2, \ldots, a_n\}$ represents a non-empty finite set of breast cancer gene characteristics, a represents the number of the breast cancer gene characteristics; $D=\{D_1, D_2\}$ represents a non-empty finite set of classification labels for the detected patients with breast cancer genes, $AT=C \cup D$ represents all gene attributes and decision attributes, $d_1$ represents that a patient has breast cancer, $d_2$ represents that a patient does not have breast cancer, and $C \cap D = \emptyset$; $V = \cap_{a \in C \cup D} V_a$, $V_a$ represents possible situations of a gene characteristic a of the detected patients with breast cancer genes; $f: U \times C \cup D \to V$ is an information function, which assigns an information value to each of the gene characteristics of the detected patients with breast cancer genes, that is, $\forall a \in C \cup D$, $x \in U$, $f(x,a) \in V_a$, where $\delta$ represents a neighborhood threshold.

In S2, unlabeled data in the data set for the breast cancer genes are normalized, and a data normalization formula is as follows:

$$x' = \frac{x - \min(x)}{\max(x) - \min(x)}, \qquad (12)$$

where x represents a value of an attribute in an original sample, x' represents a normalized value of the attribute in the original sample, max(x) represents a maximum value of the attribute in all samples, and min(x) represents a minimum value of the attribute in all samples.

In S3, an information granulation of the breast cancer gene data is implemented by adopting a K-means clustering algorithm, a number k of optimum information granules is obtained by adopting a combination of contour coefficients and a PCA dimensionality reduction, and a plurality of granularities, that is, C={$P_1$, $P_2$, . . . , $P_k$} are finally obtained.

In S4, a method for implementing an information granulation, that is, k samples of breast cancer genes are randomly selected as a cluster center. An Euclidean distance is adopted to assign each sample point to a position closest to the cluster center. A mean value of sample points in the cluster is calculated as a new cluster center for each cluster, and when a position of the cluster center no longer changes, k information granules are finally obtained.

In S5, the breast cancer gene attributes are divided into the plurality of granularities, and a self-adaptive attribute reduction of a neighborhood rough set based on a cluster center distance is implemented at each granularity, that is, by temporarily retaining gene attributes in a dense similarity region. A multi-layer neighborhood screening is performed on a large number of gene attributes outside the dense similarity region to remove irrelevant gene attributes, and then redundant gene attributes in the dense similarity region are removed by adopting a process of heuristic search iterative to a positive region to obtain important breast cancer gene attributes.

In S6, reduced breast cancer gene attributes are obtained for each granularity. The plurality of granularities are fused, and similar redundant gene attributes at different granularities are removed during the fusion process by adopting an attribute reduction of a multi-granularity neighborhood based on an attribute inclusion degree: by means of introducing a concept of the attribute inclusion degree, an optimum multi-granularity neighborhood radius under the breast cancer gene data is obtained by refining a learning curve of the attribute inclusion degree, and the redundant gene attributes at different granularities are removed based on a multi-granularity neighborhood radius by adopting the heuristic search, so as to finally obtain a reduction set of the attributes.

In S7, the attribute reduction set is fitted by adopting a SVM support vector machine, an accuracy rate and a recall rate are introduced as two indicators. To comprehensively consider a stability of a model, a penalty is introduced on the basis of adopting the SVM support vector machine as a classifier of the model to make the classification model have the good accuracy rate and the recall rate at the same time, that is, a classification prediction based on breast cancer gene data under this model has a high accuracy rate and a low risk of predicting a cancer patient as a normal person.

In S8, large-scale breast cancer gene data are input, appropriate attributes are selected by using the reduction set, and the final prediction results are obtained by using the classifier.

In the method for classifying the multi-granularity breast cancer genes based on the double self-adaptive neighborhood radius, wherein the step of S3 specifically includes the following steps.

In Step S3.1, the clustering algorithm is evaluated by adopting the contour coefficients, and when a similarity between an i-th breast cancer gene attribute and other breast cancer gene attributes in the cluster is $a_i$ and a similarity between the i-th breast cancer gene attribute and other breast cancer gene attributes outside the cluster is $b_i$, contour coefficients of the i-th breast cancer gene attribute are defined as follows:

$$s_i = \frac{b_i - a_i}{\max(a_i, b_i)}, \quad (13)$$

where a value range of $s_i$ is [−1,1], the closer a contour system to 1 is, the better a clustering effect is, and when the contour coefficients are negative, the clustering effect is poorer.

In Step S3.2, simplifying is performed to reduce the breast cancer gene data by adopting an algorithm of the PCA dimensionality reduction based on a principal component analysis, to implement visualization of the dimensionality reduction, and an actual effect on clustering is tested in combination with the clustering algorithm, which specifically includes as follows.

For m n-dimensional breast cancer gene data, a relationship design covariance matrix between variables is as follows:

$$\text{cov Matrix} = \frac{1}{m-1} \begin{bmatrix} \text{cov}(c_1, c_1) & \text{cov}(c_1, c_2) & \ldots & \text{cov}(c_1, c_n) \\ \text{cov}(c_2, c_1) & \text{cov}(c_2, c_2) & \ldots & \text{cov}(c_2, c_n) \\ \vdots & \vdots & \ldots & \vdots \\ \text{cov}(c_n, c_1) & \text{cov}(c_n, c_2) & \ldots & \text{cov}(c_n, c_n) \end{bmatrix}, \quad (14)$$

where $\text{cov}(c_i, c_j)$ represents a covariance between an i-th attribute and a j-th attribute.

A contribution rate θ and a cumulative contribution rate Θ of the covariance matrix are calculated then according to an eigenvalue:

$$\theta_i = y_i / \sum_{n=1}^{N} y_n, i = 1, 2 \ldots, N, \quad (15)$$

where N is a total of gene attributes, $y_i$ is an eigenvalue of an i-th column, and $y_n$ is an eigenvalue of an n-th column $$\Theta_r = \sum_{i=1}^{r} \theta_i, \quad (16)$$

where $\theta_i$ represents a contribution rate of the i-th column in the covariance matrix, and $\Theta_r$ represents a cumulative contribution rate of first r columns in the covariance matrix.

In Step S3.3, the first r dimensions of the covariance matrix are taken as a projection matrix $S_{n \times r}$, and a reduced-dimensional matrix $Y_{m \times n}$ is multiplied by the projection matrix $S_{n \times r}$ to obtain a reduced-dimensional matrix $T_{m \times r}$, that is $$Y_{m \times n} \times S_{n \times r} = T_{m \times r} \quad (17),$$

where m represents a number of samples of the breast cancer gene data, n represents a number of original gene attributes in the breast cancer gene data, and r represents a number of gene attributes in the breast cancer gene data obtained after the dimensionality reduction.

In Step S3.4, a rough value interval for a value k is determined by the contour coefficients, then an optimum value k is selected by refining the interval through a method of a PCA dimensionality reduction visualization, and the number of information granules is obtained.

In the method for classifying the multi-granularity breast cancer genes based on the double self-adaptive neighborhood radius, the step of S5 includes specifically following steps.

In Step S5.1, a neighborhood relationship of each breast cancer gene sample $x_i$ on B under a single gene attribute is calculated at a single information granularity:

$$n_B(x_i)=\{x\in U|\Delta_B(x_i, x)\leq\delta\} \quad (18)$$

where $\Delta_B$ is a distance function, and $\delta$ is a neighborhood radius, and $\delta>0$.

In Step S5.2, a positive region of a decision attribute D of the breast cancer gene with respect to a single gene attribute B is calculated at a single information granularity:

$$NPOS_B(D) = \bigcup_{D_j\in U/D} \underline{N}B(D_j), \quad (19)$$

then a dependency of the decision attribute D with respect to B is defined as:

$$r(B, D) = \frac{|NPOS_B(D)|}{|U|}. \quad (20)$$

In Step S5.3, at a single granularity having z gene attributes of $P=\{a_1,a_2,\ldots,a_z\}$, a cluster center coordinate under the information granule is expressed as $(b_1,b_2,\ldots,b_n)$, and a cluster center coordinate of a cluster of a next nearest information granule is calculated and obtained as $(d_1, d_2, \ldots, d_n)$, where i, j are sample traversal sequence numbers that are initially 0, and $0\leq i, j\leq m$.

In Step S5.4, at a single granularity for any breast cancer gene attribute $a_t$, distance of which to a cluster center of the information granule is marked as $S_t$, and when $S_t<2\sqrt{(b_i-d_i)^2+(b_j-d_j)^2}$, the attribute is defaulted to be a breast cancer gene attribute in the dense similarity region. A set is firstly initialized as $set_i=\emptyset$ to retrieve a lower approximation set of a gene attribute i. A distance from $x_i$ to other points $x_j$ is calculated starting from $x_i$ under the attribute, and the distance from $x_i$ to $x_j$ is marked as W. When $W<(b_i-b_j)+\sqrt{2[(b_i-d_i)^2+(b_j-d_j)^2]}$ that is a neighborhood radius, $set_i=set_i\cup x_i\cup x_j$, and $set_i$ are finally obtained after traversing each point, where the decision attribute is $D=\{D_1,D_2\}$, when $set_i\subseteq D_1$ or $set_i\subseteq D_2$, $set_i$ is referred to as a lower approximation set of $x_i$ with respect to $a_t$ in $D_1$ or $D_2$ otherwise $set_i=\emptyset$.

In Step S5.5, a positive region $NPOS_{a_t}(D)=set_1\cup set_2\cup \ldots \cup set_m$ of the breast cancer gene decision attribute D with respect to $a_m$ is obtained, and the dependency of the breast cancer gene decision attribute D on a breast cancer gene condition attribute $a_t$ is calculated as follows:

$$r(a_t, D) = \frac{|NPOS_{a_t}(D)|}{|U|}.$$

In Step S5.6, dependencies of the attributes are sorted in a descending order in a list list at a single granularity, and a positive region $NPOS_p(D)$ of the breast cancer gene decision attribute D with respect to a gene attribute at a granularity P is obtained:

$$NPOS_p(D)=NPOS_{a_1}(D)\cup NPOS_{a_2}(D)\cup \ldots \cup NPOS_{a_z}(D) \quad (21).$$

In Step S5.7, a dependency $$r(P, D) = \frac{|NPOS_P(D)|}{|U|}$$

of the decision D on a condition attribute P is calculated, and $R_0=\emptyset$ is initialized.

In Step S5.8, the algorithm is ended, when $r(R_0, D)=r(P, D)$, and a final large-scale reduction set $R=R_0$ of the breast cancer genes is obtained.

In Step S5.9, when $r(R_0, D)\neq r(P, D)$, an attribute with a greatest dependency in the list is put into $R_0$, and then it jumps to Step S5.8.

In the method for classifying the multi-granularity breast cancer genes based on the double self-adaptive neighborhood radius, the step of S6 specifically includes following steps.

In Step S6.1, a decision table $S=(U,C\cup D,V, f)$ is obtained in a plurality of granularities, where $C=\{P_1, P_2, \ldots, P_k\}$, $U=\{x_1, x_2, \ldots, x_m\}$, and $D=\{D_1, D_2\}$, where k is a number of information granules, and m is a number of samples of the breast cancer gene data. An optimum neighborhood radius is selected based on the attribute inclusion degree, wherein i, j are sample traversal sequence numbers that are initially 0, and $0\leq i, j\leq m$.

In Step S6.2, for any information granule $P_t$, a set is firstly initialized as $set_i=\emptyset$ to retrieve a lower approximation set of a gene attribute i, an Euclidean distance from $x_i$ to other points $x_j$ is calculated starting from $x_i$ under the information granule, and when the Euclidean distance from $x_i$ to the other points $x_j$ is less than the neighborhood radius, $set_i=set_i\cup x_i\cup x_j$, and $set_i$ is finally obtained after traversing each point, where the decision attribute is $D=\{D_1,D_2\}$, when $set_i\subseteq D_1$ or $set_i\subseteq D_2$, $set_i$ is referred to as a lower approximation set of $x_i$ with respect to $P_t$ in $D_1$ or $D_2$ otherwise $set_i=\emptyset$.

In Step S6.3, a positive region $NPOS_{P_t}(D)=set_1\cup set_2\cup \ldots \cup set_m$ of the decision attribute D with respect to $P_t$ is obtained, and the dependency $$r(a_t, D) = \frac{|NPOS_{a_t}(D)|}{|U|}$$

of the decision attribute D on a breast cancer gene condition attribute $P_t$ is calculated.

In Step S6.4, dependencies of the breast cancer gene attributes are sorted in a descending order in a list All_list, and an optimistic multi-granularity positive region $NPOSV_C^{OPT}(D)$ of the decision attribute D with respect to C is obtained as follows:

$$NPOS_C^{OPT}(D)=NPOS_{P_1}(D)\cup NPOS_{P_2}(D)\cup \ldots \cup NPOS_{P_k}(D) \quad (22)$$

In Step S6.5, a dependency $$r(C, D) = \frac{|NPOS_C^{OPT}(D)|}{|U|}$$

of the decision D on a condition attribute C is calculated, and $Red_0=\emptyset$ is initialized.

In Step S6.6, when $r(Red_0,D)=r(C,D)$, the algorithm is ended, and a final reduction set $Red=Red_0$ of the breast cancer genes is obtained.

In Step S6.7, when $r(Red_0,D) \neq r(C,D)$, an attribute with a greatest dependency in the list All_list is put into $Red_0$, and then it jumps to Step S6.6.

In Step S6.8, an attribute $a_{t_{max}}$ with the greatest neighborhood dependency in $P_t$ is selected from Red=$\{P_i, \ldots P_j\}$ sequentially, and when $r(a_{t_{max}}, D) = r(C,D)$, the algorithm is ended, and $R = R_0$ is obtained.

In Step S6.9, when $r(R_0, D) \neq r(C,D)$, an breast cancer gene attribute with a greatest dependency $P_{t+1}$ in Red=$\{P_i \ldots P_j\}$ is put into $R_0$, and then it jumps to S6.8.

Compared with the prior art, the beneficial effects of the present disclosure lie in the following.

(1) The classifier of the present disclosure, which operates with a high accuracy rate and a high recall rate can effectively utilize the breast cancer reduction set based on the double self-adaptive neighborhood radius, and provide a detected person to obtain detection results with a high accuracy rate in a short time. Compared with other classification methods, the high recall rate model can also ensure that the high risk of a cancer patient being predicted as a normal person is minimized. Finally, it can effectively help doctors to reduce the difficulty for early diagnosis of breast cancer through the data analysis, the attribute reduction and the machine learning classification algorithm under the big data, in combination with certain clinical experience of doctors, and a patient can get an optimum treatment timing by an early cancer screening of breast cancer.

(2) The present disclosure can analyze data of a small number of samples and extract the more important gene attributes through the attribute reduction to reduce the interference of noise data on the model prediction. Compared with manually setting the neighborhood radius, the double self-adaptive neighborhood radius is adopted to improve the self-learning of the classifier to fit the model, thereby further improving the detection accuracy, and the gene prediction can be effectively performed through the above examples.

(3) The present disclosure removes a large number of redundant gene data and noise gene data through the method for classifying the multi-granularity breast cancer genes based on the double self-adaptive neighborhood radius, thereby reducing the originally detected 24481 gene attributes to 2734 gene attributes from the above examples, and at the same time, a ten-fold cross validation method can effectively solve the problems of a small number of samples and a long running time, which greatly reduces the complexity of the model and the time complexity of the algorithm, and therefore, the user can get the results in just a few minutes after submitting the to-be-detected gene data, thereby giving the detected person a better detection experience.

(4) It tends to ignore the problem of recall rate for samples. The risk of predicting a cancer patient as a normal person is extremely large, and it is likely for the detected person to miss the optimum treatment timing, whereas in the present disclosure, the model is adjusted in fully consideration of the risk problem of the detection accuracy rate and detection recall rate through the method for classifying the multi-granularity breast cancer genes based on the double self-adaptive neighborhood radius, and the model is improved by setting a penalty item, in full consideration of the influence of the recall rate on the model on the basis of ensuring a high accuracy rate of the model, thereby greatly reducing the occurrence of this kind of risk.

DETAILED DESCRIPTION OF THE EMBODIMENTS

In order to make the objectives, technical solutions and advantages of the present disclosure clearer, the present disclosure will be further described in detail below with reference to the embodiments. Certainly, the specific embodiments described herein are only used to explain the present disclosure, but not to limit the present disclosure.

Embodiment 1

Figure 1:
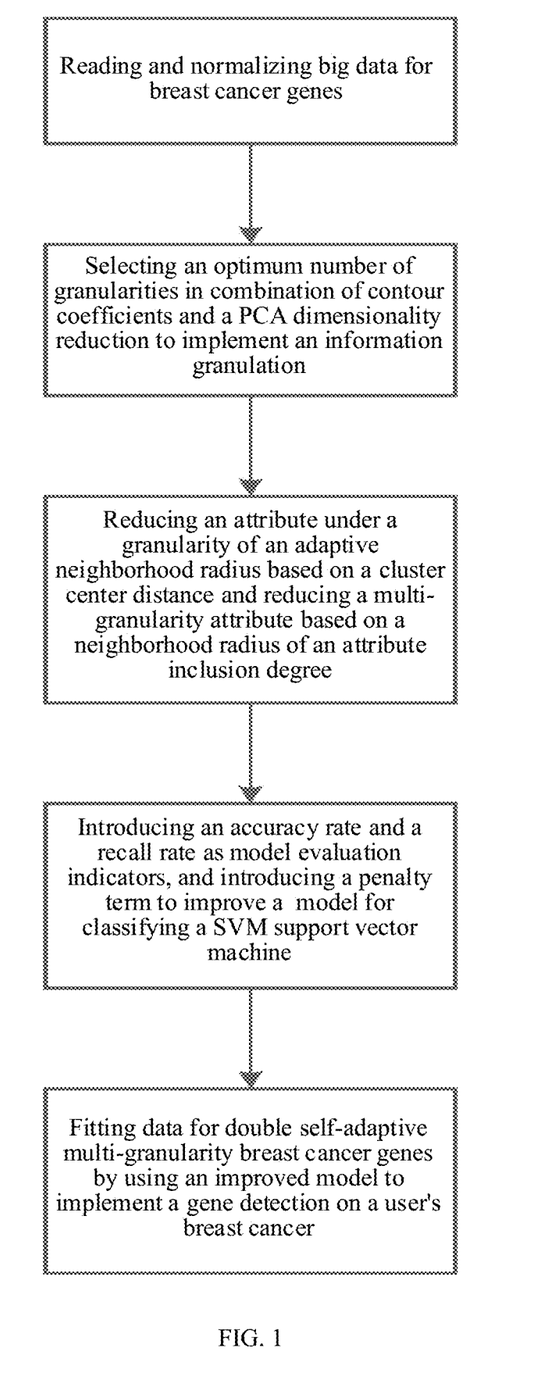
FIG. 1 illustrates a flow chart of a breast cancer gene detection according to the present disclosure.

With reference to FIGS. 1 to 5, the technical solution provided in the present disclosure is a method for classifying multi-granularity breast cancer genes based on a double self-adaptive neighborhood radius, which includes the following steps:

In Step 1, a data set for breast cancer genes are read, and data are converted into a four-tuple decision information system $S=(U,AT,V,f,\delta)$, and a neighborhood decision information system S is expressed as follows:

$S=(U,AT,V,f,\delta)$, where $U=\{x_1, x_2, x_3, \ldots, x_m\}$ represents an object set of detected patients in the data set for breast cancer genes, m represents a number of the detected patients with breast cancer genes; $C=\{a_1,a_2, \ldots, a_n\}$ represents a non-empty finite set of breast cancer gene characteristics, n represents the number of the breast cancer gene characteristics; $D=\{D,D_2\}$ represents a non-empty finite set of classification labels for the detected patients with breast cancer genes, $AT=C \cup D$ represents all gene attributes and decision attributes, $d_1$ represents that a patient has breast cancer, $d_2$ represents that a patient does not have breast cancer, and $C \cap D = \emptyset$; $V = \cap_{a \in C \cup D} V_a$, $V_a$ represents possible situations of a gene characteristic a of the detected patients with breast cancer genes; $f: U \times C \cup D \to V$ is an information function, which assigns an information value to each of the gene characteristics of the detected patients with breast cancer genes, that is, $\forall a \in C \cup D, x \in U$, $f(x,a) \in V_a$, where $\delta$ represents a neighborhood threshold.

The data set for breast cancer genes is adopted to test the above model, in which there are 97 samples, a total of 24481 gene attributes, and two types of decision attributes, namely, diagnosed breast cancer patients and normal persons.

In Step 2, unlabeled data in the data set for breast cancer genes are normalized, and a data normalization formula is as follows:

$$x' = \frac{x - \min(x)}{\max(x) - \min(x)}, \quad (23)$$

where x represents a value of an attribute in an original sample, x' represents a normalized value of the attribute in the original sample, max(x) represents a maximum value of the attribute in all samples, and min(x) represents a minimum value of the attribute in all samples.

In Step 3, an information granulation of the breast cancer gene data is implemented by adopting a K-means clustering algorithm. A number k of optimum information granules is obtained by adopting a combination of contour coefficients and a PCA dimensionality reduction, and a plurality of granularities, that is, C={$P_1$, $P_2$, . . . , $P_k$}, are finally obtained.

In Step 4, a method for implementing an information granulation: k samples of breast cancer genes are randomly selected as a cluster center, an Euclidean distance are adopted to assign each sample point to a position closest to the cluster center, a mean value of sample points in the cluster is calculated as a new cluster center for each cluster, and when a position of the cluster center no longer changes, k information granules are finally obtained.

The optimum granularity number, that is, the value k, is determined within an interval proximate to k=90 by the contour coefficient index, and then it is most reasonable to determine 90 granularities, that is, k=90, for the division by the PCA dimensionality reduction visualization.

Figure 2:
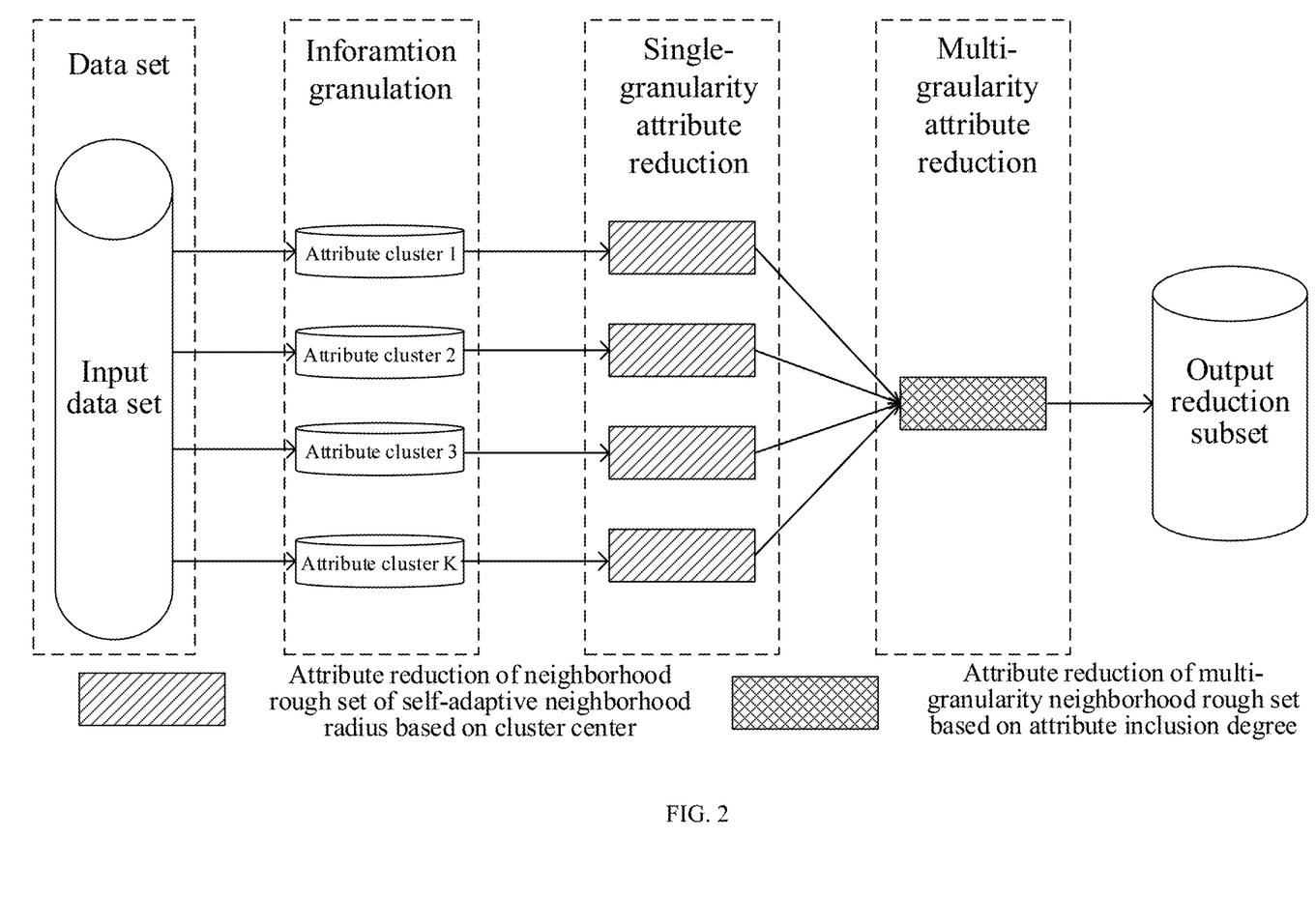
FIG. 2 illustrates a flowchart of a multi-granularity attribute reduction of a double self-adaptive neighborhood radius based on breast cancer gene data according to the present disclosure.
Figure 4:
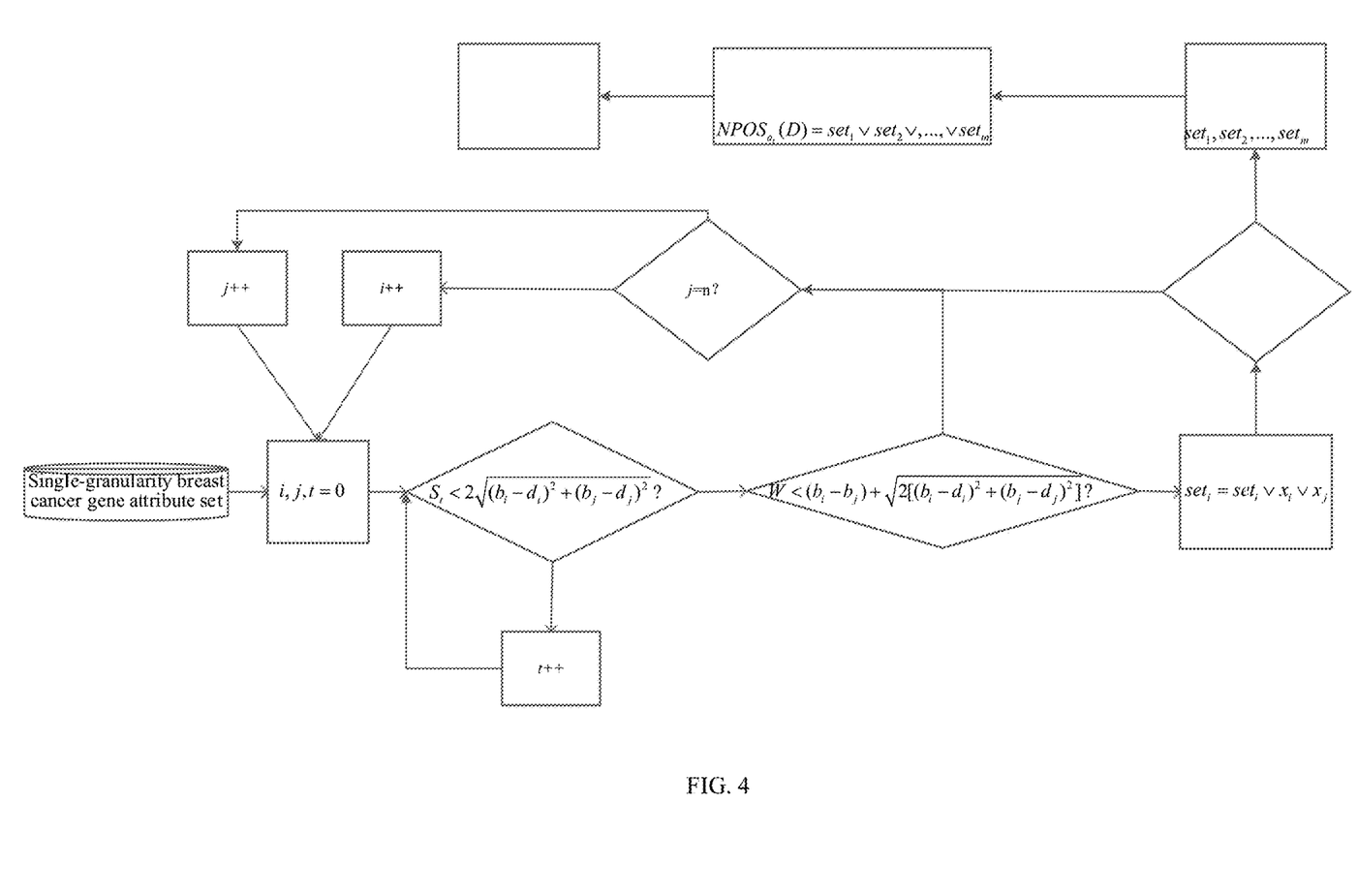
FIG. 4 illustrates a flowchart of an attribute reduction of a single-granularity self-adaptive neighborhood radius under the breast cancer gene data according to the present disclosure.

In Step 5, the breast cancer gene attributes are divided into the plurality of granularities, and a self-adaptive attribute reduction of a neighborhood rough set based on a cluster center distance is implemented at each granularity: by temporarily retaining gene attributes in a dense similarity region, a multi-layer neighborhood screening is performed on a large number of gene attributes outside the dense similarity region to remove irrelevant gene attributes, and then redundant gene attributes in the dense similarity region are removed by adopting a process of heuristic search iterative to a positive region to obtain important breast cancer gene attributes.

At one granularity, the distances between the granularity and the cluster centers of the other 89 granularities are selected, and the cluster center with the shortest cluster center distance is selected to obtain the self-adaptive neighborhood radius to be H=h+$\sqrt{2}$Z, where Z is the shortest cluster center distance, h is a difference between the vertical coordinates of the granularity cluster center and the nearest granularity cluster center. Then, the single-granularity neighborhood attribute reduction algorithm is adopted to obtain the reduction set at this granularity, and finally the reduction sets at the remaining 89 granularities are obtained analogously.

Figure 5:
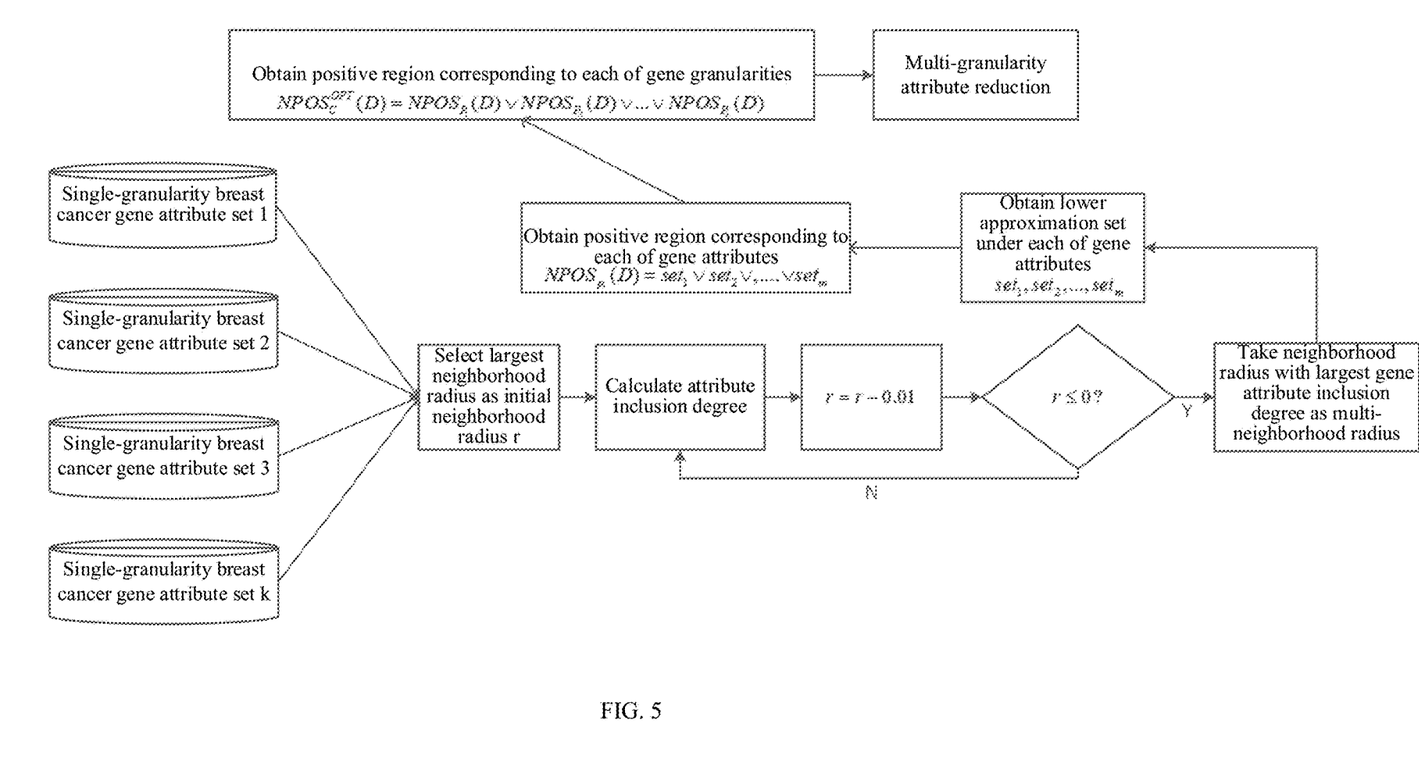
FIG. 5 illustrates a flowchart of an attribute reduction of a multi-granularity self-adaptive neighborhood radius under the breast cancer gene data according to the present disclosure.

In Step 6, reduced breast cancer gene attributes are obtained for each granularity, the plurality of granularities are fused, and by adopting an attribute reduction of a multi-granularity neighborhood based on an attribute inclusion degree, similar redundant gene attributes at different granularities are removed during the fusion process: a concept of the attribute inclusion degree is introduced, by refining a learning curve of the attribute inclusion degree, an optimum multi-granularity neighborhood radius under the breast cancer gene data is obtained, the redundant gene attributes at different granularities are removed based on a multi-granularity neighborhood radius by adopting the heuristic search, and a reduction set of the attributes is finally obtained.

The neighborhood radii at all granularities are selected, and the largest neighborhood radius of 0.2 is selected as the initial multi-granularity neighborhood radius, that is, the value range of the multi-granularity neighborhood radius is [0,0.2]. The attribute inclusion degree under each multi-granularity neighborhood radius is calculated with a step size of 0.01, and the neighborhood radius with the largest attribute inclusion degree, that is, 0.13, is selected as the multi-granularity neighborhood radius. Finally, the multi-granularity neighborhood attribute reduction algorithm is adopted to fuse 90 granularities to obtain a final reduction set with a total of 2734 gene attributes.

Figure 3:
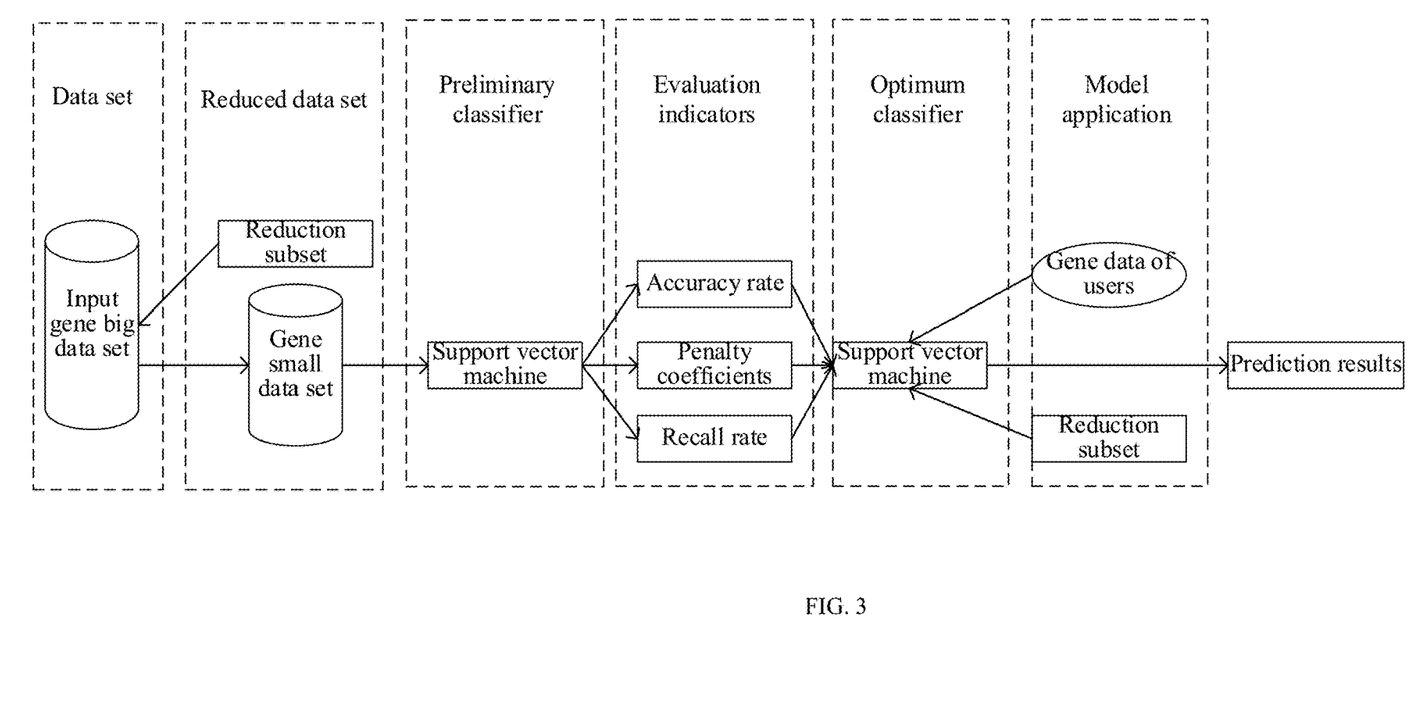
FIG. 3 illustrates a flowchart of a classification and detection of the breast cancer gene data according to the present disclosure.

In Step 7, the attribute reduction set is fitted by adopting a SVM support vector machine, an accuracy rate and a recall rate are introduced as two indicators, and in comprehensive consideration of a stability of a model, a penalty is introduced on the basis of adopting the SVM support vector machine as a classifier of the model to make the classification model have the good accuracy rate and the recall rate at the same time, that is, a classification prediction based on the breast cancer gene data under this model has a higher accuracy rate and a lower risk of predicting a cancer patient as a normal person.

The ten-fold cross method is adopted to randomly select 90% of the samples as the training set and 10% of the samples as the test set to divide the samples. The SVM support vector machine classification algorithm is adopted to fit the samples with 10 times trainings in total, of which the correct rate is over 90% for 7 times, and the average correct rate is about 85.7%. By introducing the penalty item to improve the model, and at the same time considering the recall rate, the average correct rate of the model prediction is eventually about 91.2%, and the recall rate is about 82%.

In Step 8, large-scale breast cancer gene data are input, appropriate attributes are selected by using the reduction set, and the final prediction results are selected by using the classifier.

In the method for classifying the multi-granularity breast cancer genes based on the double self-adaptive neighborhood radius, the step of S3 specifically includes the following steps.

In Step S3.1, the clustering algorithm is evaluated by adopting the contour coefficients, and when a similarity between an i-th breast cancer gene attribute and other breast cancer gene attributes in the cluster is $a_i$ and a similarity between the i-th breast cancer gene attribute and other breast cancer gene attributes outside the cluster is $b_i$, the contour coefficients of the i-th breast cancer gene attribute are defined as follows:

$$s_i = \frac{b_i - a_i}{\max(a_i, b_i)}, \quad (24)$$

where a value range of $s_i$ is [−1,1], the closer a contour system to 1 is, the better a clustering effect is, and when the contour coefficients are negative, the clustering effect is poorer;

A method for classifying multi-granularity breast cancer genes based on a double adaptive neighborhood radius is obtained by the contour coefficients.

In Step S3.2, by adopting an algorithm of the PCA dimensionality reduction based on a principal component analysis, it is simplified to reduce the breast cancer gene data to implement visualization of the dimensionality reduction, and an actual effect on clustering is tested in combination with the clustering algorithm, which specifically includes as follows.

For m n-dimensional breast cancer gene data, a relationship design covariance matrix between variables is as follows:

$$\text{cov Matrix} = \frac{1}{m-1} \begin{bmatrix} \text{cov}(c_1, c_1) & \text{cov}(c_1, c_2) & \cdots & \text{cov}(c_1, c_n) \\ \text{cov}(c_2, c_1) & \text{cov}(c_2, c_2) & \cdots & \text{cov}(c_2, c_n) \\ \vdots & \vdots & \cdots & \vdots \\ \text{cov}(c_n, c_1) & \text{cov}(c_n, c_2) & \cdots & \text{cov}(c_n, c_n) \end{bmatrix}, \quad (25)$$

where $\text{cov}(c_i, c_j)$ represents a covariance between an i-th attribute and a j-th attribute.

Then, a contribution rate θ and a cumulative contribution rate Θ of the covariance matrix are calculated according to an eigenvalue:

$$\theta_i = y_i \bigg/ \sum_{n=1}^{N} y_n, \, i = 1, 2 \ldots, N, \quad (26)$$

where N is a total of gene attributes, $y_i$ is an eigenvalue of an i-th column, and $y_n$ is an eigenvalue of an n-th column $$\Theta_r = \sum_{i=1}^{r} \theta_i, \quad (27)$$

where $\theta_i$ represents a contribution rate of the i-th column in the covariance matrix, and $\Theta_r$ represents a cumulative contribution rate of first r columns in the covariance matrix.

In Step S3.3, the first r dimensions of the covariance matrix are taken as a projection matrix $S_{n \times r}$, and a reduced-dimensional matrix $Y_{m \times n}$ is multiplied by the projection matrix $S_{n \times r}$ to obtain a reduced-dimensional matrix $T_{m \times r}$, that is $$Y_{m \times n} \times S_{n \times r} = T_{m \times r} \quad (28),$$

where m represents a number of samples of the breast cancer gene data, n represents a number of original gene attributes in the breast cancer gene data, and r represents a number of gene attributes in the breast cancer gene data obtained after the dimensionality reduction.

In Step S3.4, a rough value interval for a value k is determined by the contour coefficients, then an optimum value k is selected by refining the interval through a method of a PCA dimensionality reduction visualization, and the number of information granules is obtained.

It is most reasonable to finally determine 90 granularities, that is, k=90, for the division through the PCA dimensionality reduction visualization.

In the method for classifying the multi-granularity breast cancer genes based on the double self-adaptive neighborhood radius, the step of S5 includes specifically following steps.

In Step S5.1, a neighborhood relationship of each breast cancer gene sample x, on B under a single gene attribute is calculated at a single information granularity:

$$n_B(x_i) = \{x \in U | \Delta_B(x_i, x) \leq \delta\} \quad (29),$$

where $\Delta_B$ is a distance function, and δ is a neighborhood radius, and δ>0.

In Step S5.2, a positive region of a decision attribute D of the breast cancer gene with respect to a single gene attribute B is calculated at a single information granularity:

$$NPOS_B(D) = \bigcup_{D_1 \in U/D} NB(D_j), \quad (30)$$

Then a dependency of the decision attribute D with respect to B is defined as:

$$r(B, D) = \frac{|NPOS_B(D)|}{|U|}. \quad (31)$$

In Step S5.3, at a single granularity having z gene attributes of $P=\{a_1, a_2, \ldots, a_z\}$, a cluster center coordinate under the information granule is expressed as $(b_1, b_2, \ldots, b_n)$ a cluster center coordinate of a cluster of a next nearest information granule is calculated and obtained as $(d_1, d_2, \ldots, d_n)$, where i, j are sample traversal sequence numbers that are initially 0, and 0≤i, j≤m.

In Step S5.4, at a single granularity for any breast cancer gene attribute $a_t$, distance of which to a cluster center of the information granule is marked as $S_t$, when $S_t<2\sqrt{(b_i-d_i)^2+(b_j-d_j)^2}$, the attribute is defaulted to be a breast cancer gene attribute in the dense similarity region, a set is firstly initialized as $\text{set}_i=\emptyset$ to retrieve a lower approximation set of a gene attribute i, a distance from $x_i$ to other points $x_j$ is calculated starting from $x_i$ under the attribute, the distance from $x_i$ to $x_j$ is marked as W, and when $W<(b_i-b_j)+\sqrt{2[(b_i-d_i)^2+(b_j-d_j)^2]}$ that is a neighborhood radius, $\text{set}_i=\text{set}_i \vee x_i \vee x_j$, and set, are finally obtained after traversing each point, where the decision attribute is $D=\{D_1, D_2\}$, when $\text{set}_i \subseteq D_1$ or $\text{set}_i \subseteq D_2$, $\text{set}_i$ is referred to as a lower approximation set of $x_i$ with respect to $a_t$ in $D_1$ or $D_2$, otherwise $\text{set}_i = \emptyset$.

The neighborhood radius is obtained as $H=h+\sqrt{2}Z$, where Z is the shortest cluster center distance, and h is the difference between the vertical ordinates of the granularity cluster center and the nearest granularity cluster center.

In Step S5.5, a positive region $NPOS_{a_t}(D)=\text{set}_1 \vee \text{set}_2 \vee \ldots \vee \text{set}_m$ of the breast cancer gene decision attribute D with respect to $a_m$ is obtained, and the dependency of the breast cancer gene decision attribute D on a breast cancer gene condition attribute $a_t$ is calculated as follows:

$$r(a_t, D) = \frac{|NPOS_{a_t}(D)|}{|U|}.$$

In Step S5.6, dependencies of the attributes are sorted in a descending order in a list list at a single granularity, and a positive region $NPOS_p(D)$ of the breast cancer gene decision attribute D with respect to a gene attribute at a granularity P is obtained:

$$NPOS_p(D)=NPOS_{a_1}(D) \vee NPOS_{a_2}(D) \vee \ldots \vee NPOS_{a_z}(D) \quad (32).$$

In Step S5.7, a dependency $$r(P, D) = \frac{|NPOS_P(D)|}{|U|}$$

of the decision D on a condition attribute P is calculated, and $R_0=\emptyset$ is initialized.

In Step S5.8, the algorithm is ended, when $r(R_0, D)=r(P, D)$, and a final large-scale reduction set $R=R_0$ of the breast cancer genes is obtained.

In Step S5.9, when $r(R_0,D) \neq r(P,D)$, an attribute with a greatest dependency in the list is put into $R_0$, and then it jumps to Step S5.8.

In the method for classifying the multi-granularity breast cancer genes based on the double self-adaptive neighborhood radius, the step of S6 specifically includes following steps.

In Step S6.1, a decision table $S=(U, C \cup D, V, f)$ is obtained in a plurality of granularities, where $C=\{P_1, P_2, \ldots, P_k\}$, $U=\{x_1, x_2, \ldots, x_m\}$, and $D=\{D_1, D_2\}$, where k is a number of information granules, and m is a number of samples of the breast cancer gene data. An optimum neighborhood radius is selected based on the attribute inclusion degree, wherein i, j are sample traversal sequence numbers that are initially 0, and $0 \leq i, j \leq m$.

In this data set, k=90, m=97.

In Step S6.2, for any information granule $P_t$, a set is firstly initialized as $set_i=\emptyset$ to retrieve a lower approximation set of a gene attribute i, an Euclidean distance from $x_i$ to other points $x_j$ is calculated starting from $x_i$ under the information granule, and when the Euclidean distance from $x_i$ to the other points $x_j$ is less than the neighborhood radius, $set_i=set_i \lor x_i \lor x_j$, and $set_i$ is finally obtained after traversing each point, where the decision attribute is $D=\{D_1,D_2\}$, when $set_i \subseteq D_1$ or $set_i \subseteq D_2$, $set_i$ is referred to as a lower approximation set of $x_i$ with respect to $P_t$ in $D_1$ or $D_2$, otherwise $set_i=\emptyset$.

The largest neighborhood radius of 0.2 is selected as the initial multi-granularity neighborhood radius, that is, the value range of the multi-granularity neighborhood radius is [0,0.2]. The attribute inclusion degree under each multi-granularity neighborhood radius is calculated with a step size of 0.01, and the neighborhood radius with the largest attribute inclusion degree, that is, 0.13, is selected as the multi-granularity neighborhood radius.

In Step S6.3, a positive region $NPOS_{P_t}(D)=set_1 \lor set_2 \lor \ldots \lor set_m$ of the decision attribute D with respect to $P_t$ is obtained, and the dependency $$r(a_t, D) = \frac{|NPOS_{a_t}(D)|}{|U|}$$

of the decision attribute D on a breast cancer gene condition attribute $P_t$ is calculated.

In Step S6.4, dependencies of the breast cancer gene attributes are sorted in a descending order in a list All_list, and an optimistic multi-granularity positive region $NPOS_C^{OPT}(D)$ of the decision attribute D with respect to C is obtained as follows:

$$NPOS_C^{OPT}(D) = NPOS_{P_1}(D) \lor NPOS_{P_2}(D) \lor \ldots \lor NPOS_{P_k}(D) \quad (33)$$

In Step S6.5, a dependency $$r(C, D) = \frac{|NPOS_C^{OPT}(D)|}{|U|}$$

of the decision D on a condition attribute C is calculated, and $Red_0=\emptyset$ is initialized.

In Step S6.6, when $r(Red_0,D)=r(C,D)$, the algorithm is ended, and a final reduction set $Red=Red_0$ of the breast cancer genes is obtained.

In Step S6.7, when $r(Red_0,D) \neq r(C,D)$, an attribute with a greatest dependency in the list All_list is put into $Red_0$, and then it jumps to Step S6.6.

In Step S6.8, an attribute $a_{t_{max}}$ with the greatest neighborhood dependency in $P_t$ is selected from $Red=\{P_i, \ldots P_j\}$ sequentially. When $r(a_{t_{max}}, D)=r(C, D)$, the algorithm is ended, and $R=R_0$ is obtained.

In Step S6.9, when $r(R_0,D) \neq r(C,D)$, an breast cancer gene attribute with a greatest dependency in $P_{t+1}$ in $Red=\{P_i, \ldots P_j\}$ is put into $R_0$, and then it jumps to S6.8.

It can be seen that, although the extraction of user's gene data is mainly adopted by the current gene detection and predictions are performed by comparing hundreds of millions of data of the company, these data are not publicly available, and therefore, due to the problem of data sources, it is difficult for the gene detection method to be popularized. Only a small number of samples are provided by a plenty of published data sets, and it is difficult to achieve a higher accuracy rate for high-dimensional gene attributes, whereas in the present disclosure, the more important gene attributes can be extracted by analyzing a small number of samples to improve the detection accuracy, and gene prediction can be effectively performed through the above examples.

Moreover, many companies need to compare hundreds of millions of samples in the database with user's gene data, which brings a considerable time cost, since the time complexity of calculating all the gene attributes of the system will increase exponentially with the increase of the combinations of genes, and the user needs to wait hours or even days for final results, whereas in the present disclosure, a large amount of redundant gene data and noise gene data are removed through the method for classifying the multi-granularity breast cancer genes based on the double self-adaptive neighborhood radius, and the originally detected 24481 gene attributes are reduced to 2734 gene attributes from the above examples, which greatly reduces the time complexity of the algorithm. The results can be obtained in just a few minutes after the user submits the detected gene data, thereby giving the detected person an excellent detection experience.

In addition, many companies tend to ignore the recall rate when comparing samples, the risk of predicting a cancer patient as a normal person is extremely high, and it is likely to miss the optimum treatment timing for the detected person; whereas in the present disclosure, the risk problem of the detection accuracy rate and detection recall rate is fully considered through the method for classifying the multi-granularity breast cancer genes based on the double self-adaptive neighborhood radius, and the model is adjusted, thereby greatly reducing the occurrence of this kind of risk.

The above-mentioned embodiments are merely preferred embodiments of the present disclosure, and are not intended to limit the present disclosure. Any modification, equivalent replacement, improvement, etc. made within the spirit and principle of the present disclosure shall be included within the protection scope of the present disclosure.

What is claimed is:

1. A method for classifying multi-granularity breast cancer genes based on a double self-adaptive neighborhood radius, comprising the following steps:

S1, reading a data set for breast cancer genes, and converting data into a four-tuple decision information system S=(U, AT, V, $f$, $\delta$), wherein a neighborhood decision information system S is expressed as follows:

S=(U, AT,V, $f$, $\delta$), wherein U={$x_1$, $x_2$, $x_3$, ..., $x_m$} represents an object set of detected patients in the data set for breast cancer genes, m represents a number of the detected patients with breast cancer genes; C={$a_1$, $a_2$, ..., $a_n$} represents a non-empty finite set of breast cancer gene characteristics, n represents a number of the breast cancer gene characteristics; D={$D_1$,$D_2$} represents a non-empty finite set of classification labels for the detected patients with breast cancer genes, AT=C∪D represents all gene attributes and decision attributes, $d_1$ represents that a patient has breast cancer, $d_2$ represents that a patient does not have breast cancer, and C∪D=Ø; V=$\cap_{a \in C \cup D} V_a$, $V_a$ represents possible situations of a gene characteristic a of the detected patients with breast cancer genes; $f$:U×C∪D→V is an information function, which assigns an information value to each of the gene characteristics of the detected patients with breast cancer genes, according to ∀a∈C∪D, x∈U, $f$(x, a)∈$V_a$, wherein $\delta$ represents a neighborhood threshold;

S2, normalizing unlabeled data in the data set for breast cancer genes, wherein a data normalization formula is as follows:

$$x' = \frac{x - \min(x)}{\max(x) - \min(x)} \quad (1)$$

wherein x represents a value of an attribute in an original sample, x' represents a normalized value of the attribute in the original sample, max(x) represents a maximum value of the attribute in all samples, and min(x) represents a minimum value of the attribute in all samples;

S3, implementing, by adopting a K-means clustering algorithm, an information granulation of the breast cancer gene data, obtaining, by adopting a combination of contour coefficients and a PCA dimensionality reduction, a number k of optimum information granules, and finally obtaining a plurality of granularities, according to C={$P_1$, $P_2$, ..., $P_k$};

S4, a method for implementing an information granulation, comprising randomly selecting k samples of breast cancer genes as a cluster center, adopting a Euclidean distance to assign each sample point to a position closest to the cluster center, calculating, for each cluster, a mean value of sample points in the cluster as a new cluster center, and finally obtaining, when a position of the cluster center no longer changes, k information granules;

S5, dividing the breast cancer gene attributes into the plurality of granularities, and implementing a self-adaptive attribute reduction of a neighborhood rough set based on a cluster center distance at each granularity, and, performing, by temporarily retaining gene attributes in a dense similarity region, a multi-layer neighborhood screening on a large number of gene attributes outside the dense similarity region to remove irrelevant gene attributes, and then removing redundant gene attributes in the dense similarity region by adopting a process of heuristic search iterative to a positive region to obtain important breast cancer gene attributes;

S6, obtaining reduced breast cancer gene attributes for each granularity, fusing the plurality of granularities, and removing, by adopting an attribute reduction of a multi-granularity neighborhood based on an attribute inclusion degree, similar redundant gene attributes at different granularities during the fusion process, and, introducing a concept of the attribute inclusion degree, obtaining, by refining a learning curve of the attribute inclusion degree, an optimum multi-granularity neighborhood radius under the breast cancer gene data, removing, by adopting the heuristic search, the redundant gene attributes at different granularities based on a multi-granularity neighborhood radius, and finally obtaining a reduction set of the attributes;

S7, fitting the attribute reduction set, by adopting a SVM support vector machine, introducing an accuracy rate and a recall rate as two indicators, and introducing, in comprehensive consideration of a stability of a model, a penalty based on adopting the SVM support vector machine as a classifier of the model; and S8, inputting large-scale breast cancer gene data, selecting appropriate attributes by using the reduction set, and finally obtaining final prediction results by using the classifier.

2. The method according to claim 1, wherein S3 further comprises the following steps:

Step S3.1, evaluating with the clustering algorithm by adopting the contour coefficients, and defining, when a similarity between an i-th breast cancer gene attribute and other breast cancer gene attributes in the cluster is $a_i$ and a similarity between the i-th breast cancer gene attribute and other breast cancer gene attributes outside the cluster is $b_i$, contour coefficients of the i-th breast cancer gene attribute as follows:

$$s_i = \frac{b_i - a_i}{\max(a_i, b_i)} \quad (2)$$

wherein a value range of $s_i$ is [−1,1], the closer a contour system to 1 is, the better a clustering effect is, and when the contour coefficients are negative, the clustering effect is poorer;

Step S3.2, simplifying, by adopting an algorithm of the PCA dimensionality reduction based on a principal component analysis, to reduce the breast cancer gene data to implement visualization of the dimensionality reduction, testing an actual effect on clustering in combination with the clustering algorithm, which specifically comprises:

for m n-dimensional breast cancer gene data, a relationship design covariance matrix between variables being as follows:

$$\text{cov Matrix} = \frac{1}{m-1} \begin{bmatrix} \text{cov}(c_1, c_1) & \text{cov}(c_1, c_2) & \ldots & \text{cov}(c_1, c_n) \\ \text{cov}(c_2, c_1) & \text{cov}(c_2, c_2) & \ldots & \text{cov}(c_2, c_n) \\ \vdots & \vdots & \ldots & \vdots \\ \text{cov}(c_n, c_n) & \text{cov}(c_n, c_2) & \ldots & \text{cov}(c_n, c_n) \end{bmatrix} \quad (3)$$

wherein cov($c_i$, $c_j$) represents a covariance between an i-th attribute and a j-th attribute;

then calculating a contribution rate $\theta$ and a cumulative contribution rate $\Theta$ of the covariance matrix according to an eigenvalue:

$$\theta_i = y_i / \sum_{n=1}^{N} y_n, \quad i = 1, 2, \ldots, N \quad (4)$$

wherein N is a total of gene attributes, $y_i$ is an eigenvalue of an i-th column, $y_n$ is an eigenvalue of an n-th column $$\Theta_r = \sum_{i=1}^{r} \theta_i \quad (5)$$

wherein $\theta_i$ represents a contribution rate of the i-th column in the covariance matrix, and $\Theta_r$ represents a cumulative contribution rate of first r columns in the covariance matrix;

Step S3.3, taking the first r dimensions of the covariance matrix as a projection matrix $S_{n \times r}$, and multiplying a reduced-dimensional matrix $Y_{m \times n}$ by the projection matrix $S_{n \times r}$ to obtain a reduced-dimensional matrix $T_{m \times r}$, according to $$Y_{m \times n} \times S_{n \times r} = T_{m \cdot r} \quad (6)$$

wherein m represents a number of samples of the breast cancer gene data, n represents a number of original gene attributes in the breast cancer gene data, and r represents a number of gene attributes in the breast cancer gene data obtained after the dimensionality reduction; and Step S3.4, determining a rough value interval for a value k by the contour coefficients, then selecting an optimum value k by refining the interval through a method of a PCA dimensionality reduction visualization, and obtaining the number of information granules.

3. The method according to claim 1, wherein S5 further comprises the following steps:

Step S5.1, calculating, at a single information granularity, a neighborhood relationship of each breast cancer gene sample $x_i$ on B under a single gene attribute:

$$n_B(x_i) = \{x \in U | \Delta_B(x_i, x) \leq \delta\} \quad (7)$$

wherein $\Delta_B$ is a distance function, and $\delta$ is a neighborhood radius, and $\delta \geq 0$;

Step S5.2, calculating, at a single information granularity, a positive region of a decision attribute D of the breast cancer gene with respect to a single gene attribute B:

$$NPOS_B(D) = \bigcup_{D_j \in U/D} \underline{N}B(D_j) \quad (8)$$

then defining a dependency of the decision attribute D with respect to B as:

$$r(B, D) = \frac{|NPOS_B(D)|}{|U|}; \quad (9)$$

Step S5.3, expressing, at a single granularity having z gene attributes of $P = \{a_1, a_2, \ldots, a_z\}$, a cluster center coordinate under the information granule as $(b_1, b_2, \ldots, b_n)$, calculating and obtaining a cluster center coordinate of a cluster of a next nearest information granule as $(d_1, d_2, \ldots, d_n)$, wherein i, j are sample traversal sequence numbers that are initially 0, and $0 \leq i$, $j \leq m$;

Step S5.4, defaulting, at a single granularity for any breast cancer gene attribute $a_t$, distance of which to a cluster center of the information granule is marked as $S_t$, when $S_t < 2\sqrt{(b_i - d_i)^2 + (b_j - d_j)^2}$, the attribute to be a breast cancer gene attribute in the dense similarity region, firstly initializing a set as $set_i = \emptyset$ to retrieve a lower approximation set of a gene attribute i, calculating a distance from $x_i$ to other points $x_j$ starting from $x_i$ under the attribute, marking the distance from $x_i$ to $x_j$ as W, and when $W < (b_i - b_j) + \sqrt{2[(b_i - d_i)^2 + (b_j - d_j)^2]}$ that is a neighborhood radius, $set_i = set_i \lor x_i \lor x_j$, and finally obtaining set, after traversing each point, wherein the decision attribute is $D = \{D_1, D_2\}$, calling, when $set_i \subseteq D_1$ or $set_i \subseteq D_2$, $set_i$ as a lower approximation set of $x_i$ with respect to $a_t$ in $D_1$ or $D_2$, otherwise $set_i = \emptyset$;

Step S5.5, obtaining a positive region $NPOS_{a_t}(D) = set_1 \lor set_2 \lor \ldots \lor set_m$ of the breast cancer gene decision attribute D with respect to $a_m$, and calculating the dependency of the breast cancer gene decision attribute D on a breast cancer gene condition attribute $a_t$ as follows:

$$r(a_t, D) = \frac{|NPOS_{a_t}(D)|}{|U|};$$

Step S5.6, sorting, at a single granularity, dependencies of the attributes in a descending order in a list All_list, and obtaining a positive region $NPOS_P(D)$ of the breast cancer gene decision attribute D with respect to a gene attribute at a granularity P:

$$NPOS_P(D) = NPOS_{a_1}(D) \lor \\ NPOS_{a_2}(D) \lor \ldots \lor NPOS_{a_z}(D) \quad (10);$$

Step S5.7, calculating a dependency $$r(P, D) = \frac{|NPOS_P(D)|}{|U|}$$

of the decision D on a condition attribute P, and initializing $R_0 = \emptyset$;

Step S5.8, ending, when $r(R_0, D) = r(P, D)$, the algorithm, and obtaining a final large-scale reduction set $R = R_0$ of the breast cancer genes; and Step S5.9, putting, when $r(R_0, D) \neq r(P, D)$, an attribute with a greatest dependency in the list into $R_0$, and then jumping to Step S5.8.

4. The method according to claim 1, wherein S6 further comprises following steps:

Step S6.1, obtaining a decision table $S = (U, C \cup D, V, f)$ in a plurality of granularities, wherein $C = \{P_1, P_2, \ldots, P_k\}$, $U = \{x_1, x_2, \ldots, x_m\}$, and $D = \{D_1, D_2\}$, k is a number of information granules, and m is a number of samples of the breast cancer gene data, then selecting an optimum neighborhood radius based on the attribute inclusion degree, wherein i, j are sample traversal sequence numbers that are initially 0, and $0 \leq i$, $j \leq m$;

Step S6.2, firstly initializing, for any information granule $P_t$, a set as $set_i = \emptyset$ to retrieve a lower approximation set of a gene attribute i, calculating a Euclidean distance from $x_i$ to other points $x_j$ starting from $x_i$ under the information granule, and when the Euclidean distance from $x_i$ to the other points $x_j$ is less than the neighborhood radius, $set_i = set_i \lor x_i \lor x_j$, and finally obtaining $set_i$ after traversing each point, wherein the decision attri bute is $D=\{D_1, D_2\}$, calling, when $set_i \subseteq D_1$ or $set_i \subseteq D_2$ $set_i$ as a lower approximation set of $x_i$ with respect to $P_t$ in $D_1$ or $D_2$, otherwise $set_i=\emptyset$;

Step S6.3, obtaining a positive region $NPOS_{p_t}(D)=set_1 \bigvee set_2 \bigvee \ldots \bigvee set_m$ of the decision attribute D with respect to $P_t$, and calculating the dependency $$r(a_t, D) = \frac{|NPOS_{a_t}(D)|}{|U|}$$

of the decision attribute D on a breast cancer gene condition attribute $P_t$;

Step S6.4, sorting dependencies of the breast cancer gene attributes in a descending order in a list All_list, and obtaining an optimistic multi-granularity positive region $NPOS_C^{OPT}(D)$ of the decision attribute D with respect to C as follows:

$$NPOS_C^{OPT}(D) = NPOS_{p_1}(D) \bigvee NPOS_{p_2}(D) \bigvee \ldots \bigvee NPOS_{p_k}(D) \quad (11)$$

Step S6.5, calculating a dependency $$r(C, D) = \frac{|NPOS_C^{OPT}(D)|}{|U|}$$

of the decision D on a condition attribute C, and initializing $Red_0=\emptyset$;

Step S6.6, ending, when $r(Red_0,D)=r(C,D)$, the algorithm, and obtaining a final reduction set $Red=Red_0$ of the breast cancer genes;

Step S6.7, putting, when $r(Red_0,D) \neq r(C,D)$, an attribute with a greatest dependency in the list All_list into $Red_0$, and then jumping to Step S6.6;

Step S6.8, selecting an attribute $a_{t_{max}}$ with the greatest neighborhood dependency in $P_t$ from $Red=\{P_i, \ldots P_j\}$ sequentially, and ending, when $r(a_{t_{max}}, D)=r(C,D)$, the algorithm, and obtaining $R=R_0$; and Step S6.9, putting, when $r(R_0,D) \neq r(C,D)$, an breast cancer gene attribute with a greatest dependency $P_{t+1}$ in $Red=\{P_i, \ldots P_j\}$ into $R_0$, and then jumping to S6.8.

* * * * *